United States Patent
Chin et al.

(10) Patent No.: US 7,195,899 B1
(45) Date of Patent: Mar. 27, 2007

(54) CELL-BASED BIOSENSOR FOR HARMFUL AIRBORNE AGENTS

(75) Inventors: Wei-Chun Chin, Tallahassee, FL (US); Soonjo Kwon, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 384 days.

(21) Appl. No.: 10/798,986

(22) Filed: Mar. 12, 2004

Related U.S. Application Data (60) Provisional application No. 60/455,101, filed on Mar. 14, 2003.

(51) Int. Cl.
*C12N 11/02* (2006.01)
(52) U.S. Cl. .......................... 435/177; 435/29; 435/395
(58) Field of Classification Search ................ 435/29, 435/177, 375, 395, 402
See application file for complete search history.

(56) References Cited

U.S. PATENT DOCUMENTS 6,270,747 B1 * 8/2001 Nadel et al. ................. 424/9.2
6,541,107 B1 * 4/2003 Zhong et al. ............ 428/312.6

OTHER PUBLICATIONS

Romet-Haddad S. et al. Trachael Epithelium in Culture. Cell Biology and Toxicology 8(2)141-150, Jul.-Sep. 1992.*
Blanquart C. et al. Primary Cultures of Tracheal Epithelial Cells for the Evaluation of Respiratory Toxicity. Toxicity in Vitro 5(5/6)499-502, 1991.*
Marano F. et al. Evaluation of Toxicity of Environmental Gas Pollutants on Respiratory Epithelia. Report 1990 NTIS PB91-110841.*

* cited by examiner

*Primary Examiner*—Ralph Gitomer
(74) *Attorney, Agent, or Firm*—Allen, Dyer, Doppelt, Milbrath & Gilchrist, P.A.

(57) ABSTRACT

A method of monitoring an air atmosphere for a harmful biological or chemical agent includes providing a plurality of mammalian respiratory airway epithelial cells borne on a porous support; contacting the porous support with a cell nutrient medium and with air by positioning said porous support at an air-liquid interface between the cell nutrient liquid and the air; sampling the air atmosphere to thereby create an air flow over the air-liquid interface so that the respiratory epithelial cells borne on the porous silicone support are contacted by the sampled air; and monitoring the respiratory epithelial cells for at least one physiological parameter indicating the cells have been exposed to the harmful agent.

34 Claims, 11 Drawing Sheets

CELL-BASED BIOSENSOR FOR HARMFUL AIRBORNE AGENTS

RELATED APPLICATION

This application claims priority from co-pending provisional application Ser. No. 60/455,101, which was filed on Mar. 14, 2003, and which is incorporated herein by reference in its entirety.

FIELD OF THE INVENTION

The present invention relates to the field of environmental monitoring and, more particularly, to environmental monitoring by using cultured mammalian cells to indicate presence of a harmful biological or chemical agent in an air atmosphere.

BACKGROUND OF THE INVENTION

Today 220 million Americans (80% of the US population) live in and around major cities (U.S. Census, 2000). Due to their high density of population and economic activities, US cities and their residents have become the primary object of terrorism schemes that aim to cause mass destruction and casualties (National Research Council, 2002).

Many biological and chemical warfare agents can be effectively spread to very large areas and affect many people through the air. These airborne harmful agents are particularly destructive in densely populated areas. such as shopping malls, subways, office buildings or stadiums. Due to their capacity to spread to large areas, airborne biological and chemical warfare agents are also the likely harmful agents that US troops will encounter in the battlefield abroad. In the War Against Terrorism, the development of sensitive devices to detect airborne harmful agents is critical for the protection of civilians in the US and our military personnel abroad.

Cell-based sensors provide sensitive and broadband detection of toxic agents without the specificity associated with traditional chemical sensors. Cell-based sensors can react to toxins similarly to "human" responses, providing an excellent first line screening device for harmful agents. The sensitivity and accuracy of cell-based sensors are primarily dependent on the physiology of the cells in the sensors. Cells with native (normal) physiology will provide better responses for sensors as their reactions to toxins resemble more closely the effects on a "whole" human, however, for direct gas sample testing, most types of cells cannot maintain normal physiology in the air-fluid interface (direct air contact) due to the fact that most cells function and live in the aqueous environment of the body.

Respiratory epithelial cells forming the lining of airway systems provide the first line of protection and responses for many inhaled harmful agents such as dust, air pollutants, chemicals and microbes as well as biological and chemical warfare agents. These airway epithelial cells reside in the interface of air and body fluid anc can maintain normal physiological functions in this unique environment. These unique properties of respiratory epithelial cells make them an ideal candidate for cell-based biosensors capable of detecting airborne harmful agents.

SUMMARY OF THE INVENTION

With the foregoing in mind, the present invention advantageously provides a method of monitoring an air atmosphere for a harmful biological or chemical agent. The method comprises providing a plurality of mammalian respiratory airway epithelial cells borne on a porous support. The porous support is contacted with a cell nutrient medium and with air by positioning said porous support at an air-liquid interface between the cell nutrient liquid and the air. Sampling the air atmosphere is conducted to thereby create an air flow over the air-liquid interface so that the respiratory epithelial cells borne on the porous silicone support are contacted by the sampled air. Finally, the method calls for monitoring the respiratory epithelial cells for at least one physiological parameter indicating the cells have been exposed to the harmful agent.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided solely for exemplary purposes so that this disclosure will be thorough and complete, and will fully convey the scope of the invention to those skilled in the art. Other features and advantages of the invention will be apparent from the following detailed description, and from the claims.

The source for the primary airway epithelial cells used in this project is New Zealand White rabbits. The Animal Care and Use Committee at Florida State University has reviewed and approved this animal use protocol (Protocol #20020127). Using primary cells from rabbits can reduce biohazardous risks associated with human samples. Additionally, human cells are costly and difficult to obtain. Rabbits provide a steady, safe and inexpensive source for this project. Rabbit airway epithelial cells were used in our previous work and were found to function and respond similarly to human airway cells (Rivera, 1962; Wanner et al., 1996; Nguyen et al., 1998; Chin et al., 2002).

Figure 1:
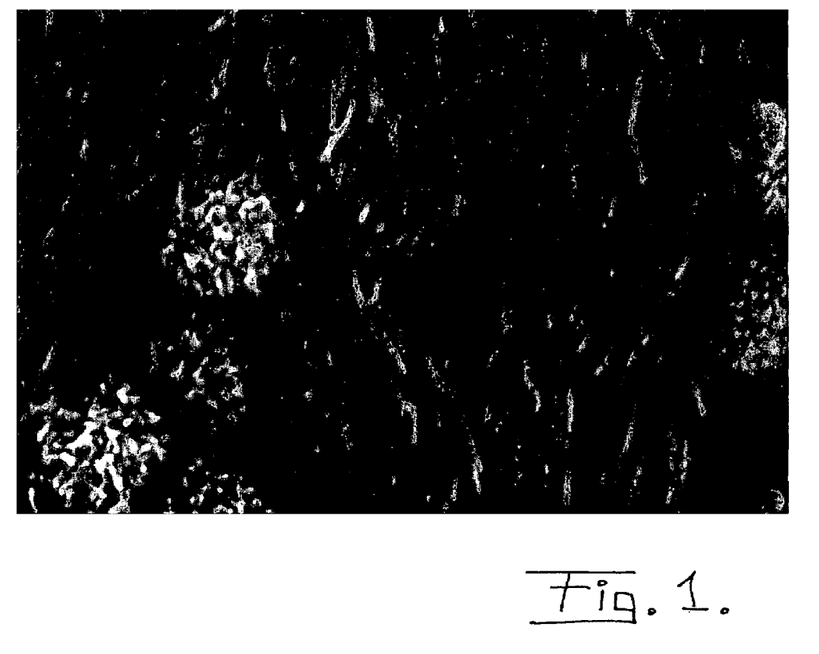
FIG. 1 is a photomicrograph showing airway ciliated cells and goblet cells used in the method according to an embodiment of the present invention.
Figure 2:
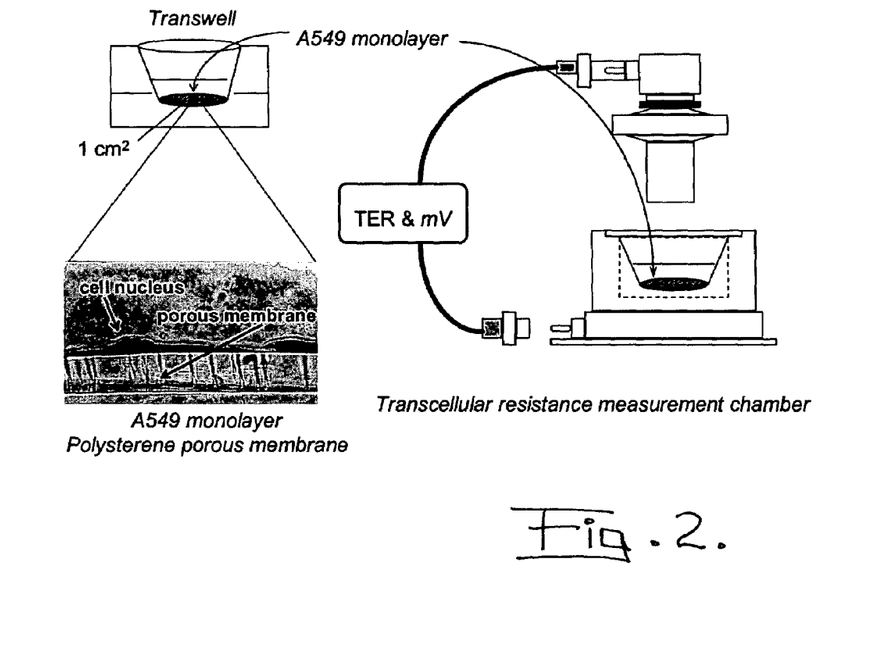
FIG. 2 is a schematic diagram of a micro-fluidic device for measuring an electrical physiologic parameter in the cells of FIG. 1.
Figure 3:
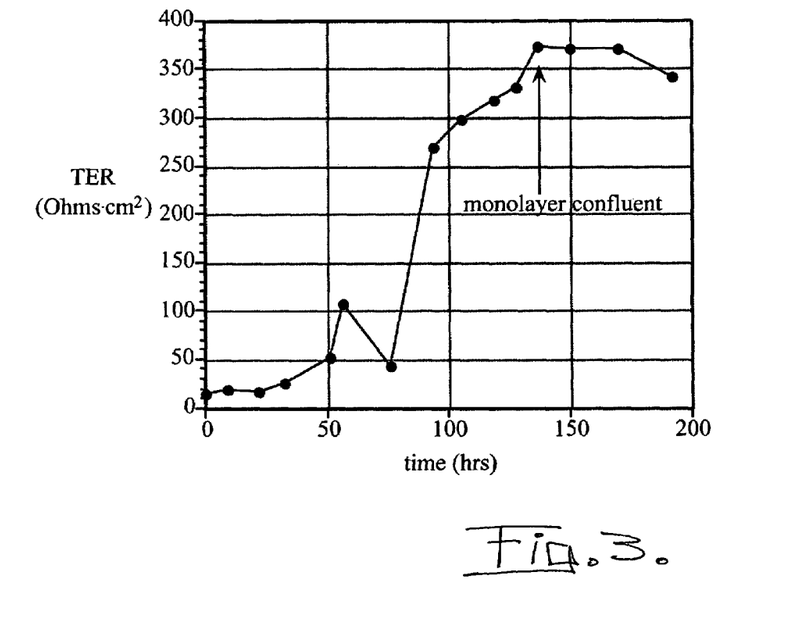
FIG. 3 is a graph showing transepithelial electrical resistance across a monolayer of the cells of the invention.
Figure 4:
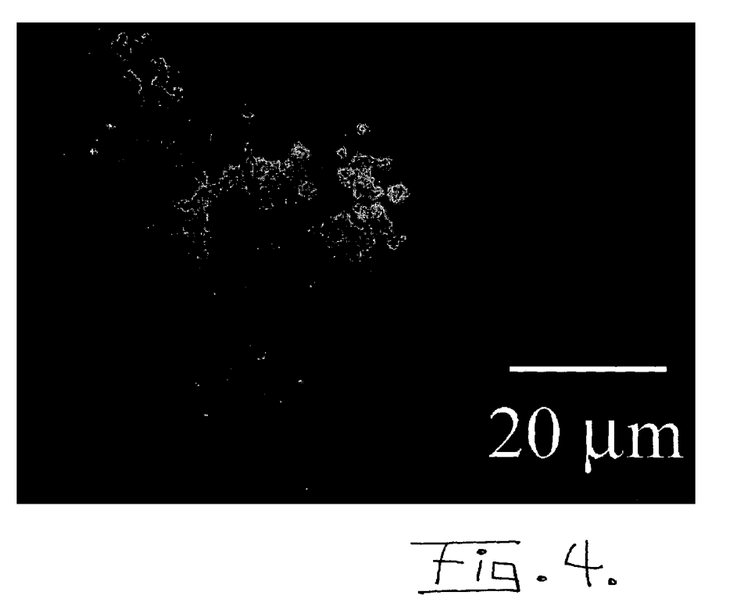
FIG. 4 is a darkfield photomicrograph using UV to show accumulation of quinacrine in mucin secretory granules of goblet cells.
Figure 5:
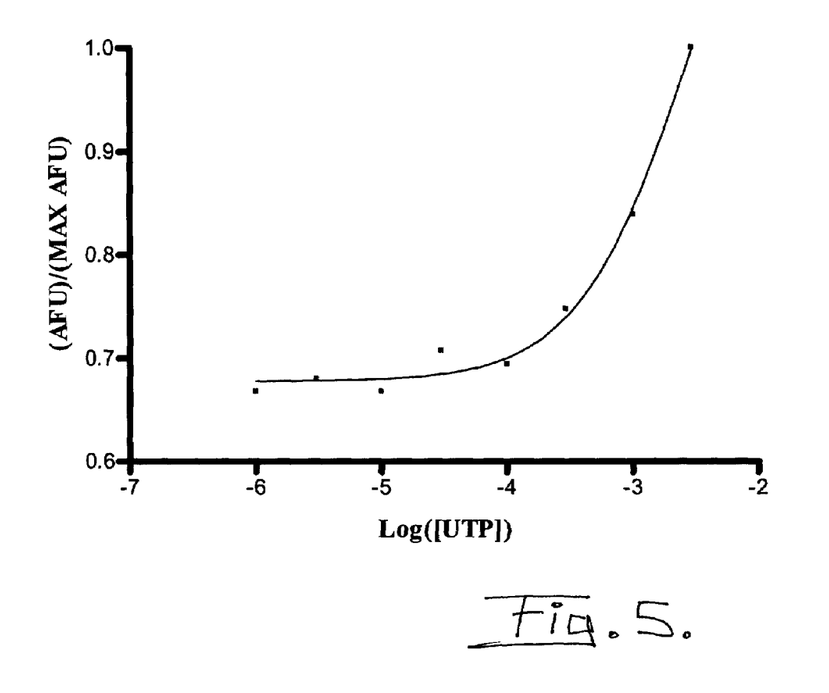
FIG. 5 is a graph showing concentration-dependence of UTP-induced mucin exocytosis in normal goblet cells.
Figure 6:
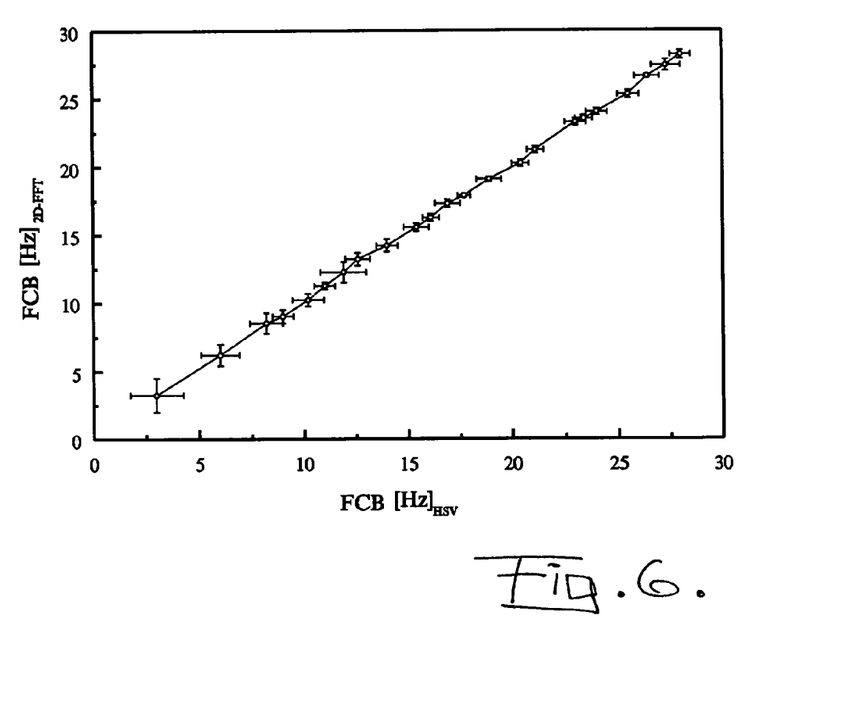
FIG. 6 shows a graph of ciliary beating frequency (CBF) of ciliated respiratory airway epithelial cells.
Figure 7:
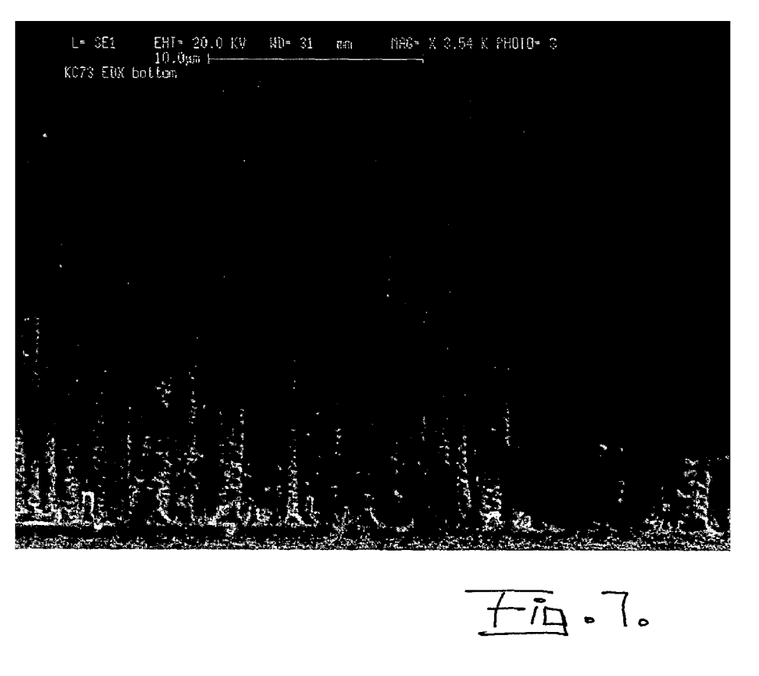
FIG. 7 is a scanning electron micrograph of generally cylindrical nanopores in a silicone support according to the invention.
Figure 8:
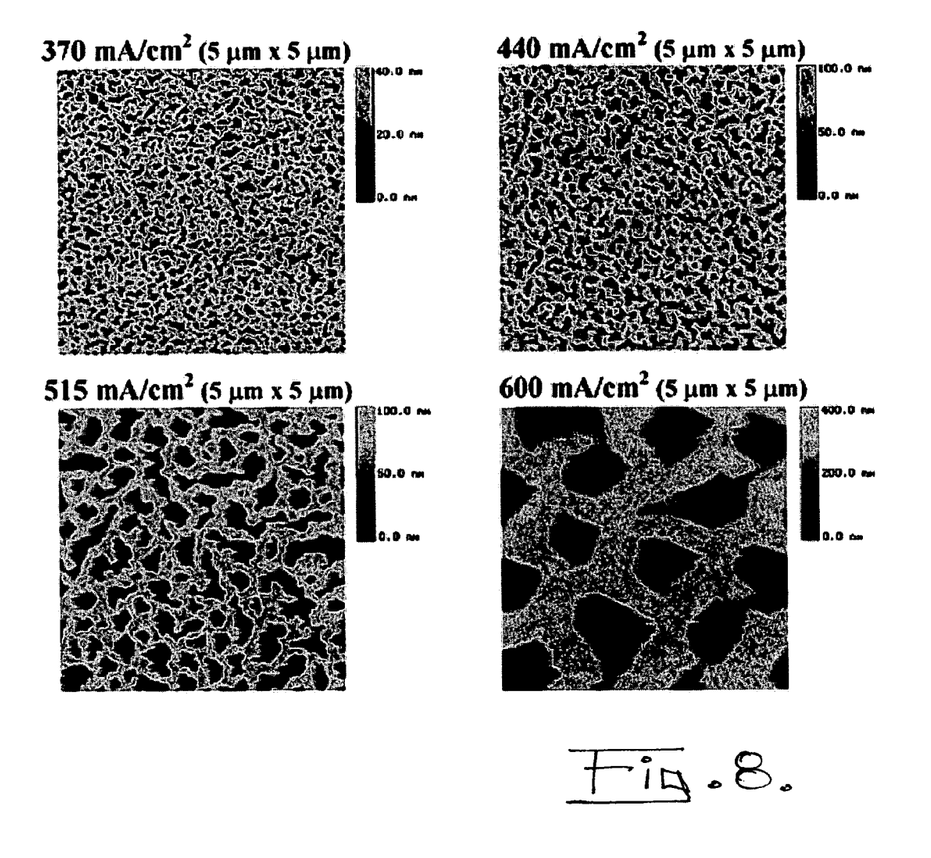
FIG. 8 shows various pore sizes as they vary with an applied current in forming the silicone support.
Figure 9:
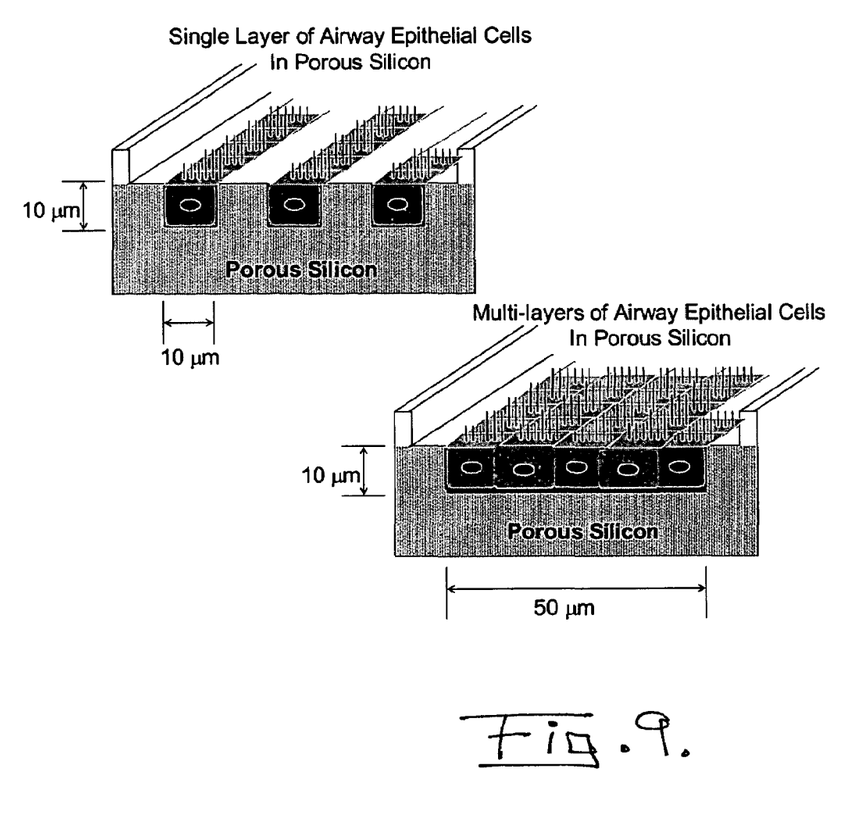
FIG. 9 shows perspective views of airway epithelial cells seeded into channels on a silicon support.
Figure 10:
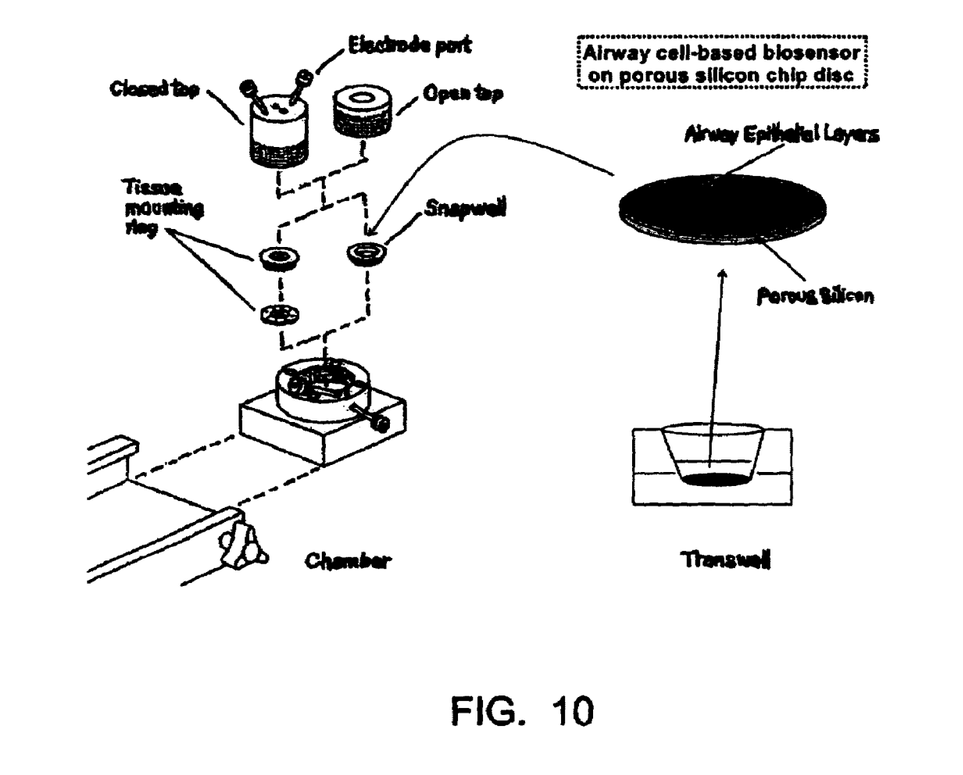
FIG. 10 is a schematic diagram of the general method of the present invention.
Figure 11:
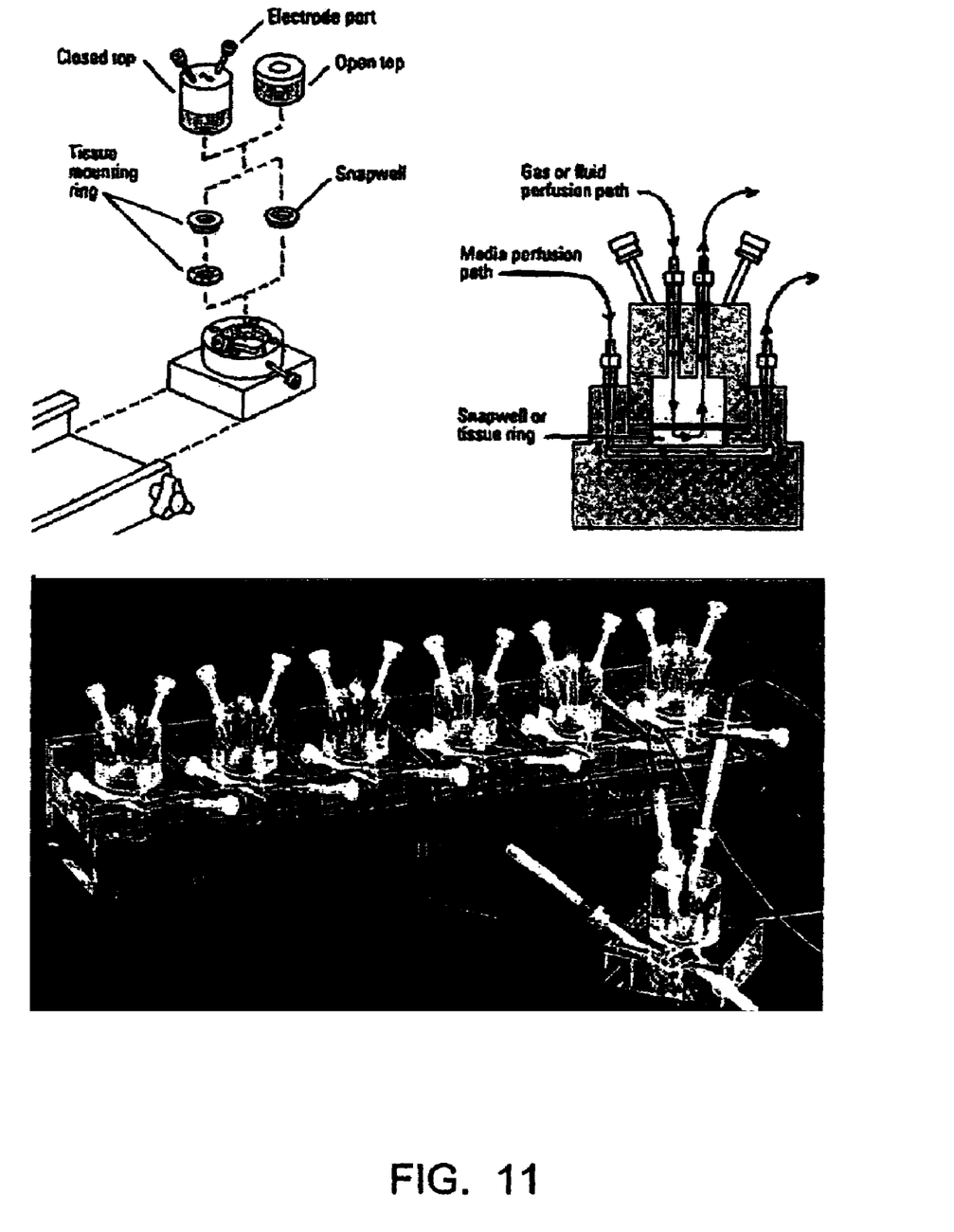
FIG. 11 shows a schematic of a device for measuring physiological parameters of the cells.

To more clearly convey the invention, the figures illustrate various aspects of the biosensor, as follows. FIG. 1 shows airway ciliated cells and goblet cells observed with a scanning electron microscope (SEM). Cilia on the surface of ciliated cells and secreted mucin from goblet cells are clearly shown. In FIG. 2 are shown airway epithelial cells at an air-liquid interface, and a measuring device for their physiological properties (i.e. transepithelial electrical resistance). FIG. 3 shows a line graph depicting transepithelial electrical resistance (Ohms/cm$^2$) across a monolayer of A549 cells grown on a polyester membrane support. FIG. 4 shows that quinacrine stain was accumulated specifically inside mucin secretory granules of the airway goblet cells. Cells were stained in 100 µM quinacrine for 5 minutes. The concentration-dependence of UTP-induced mucin exocytosis in normal tracheal goblet cells is shown in FIG. 5. The concentration-dependence curves were reproduced in triplicate. The secretion of mucin was monitored with quinacrine fluorescence. Data were fit as a sigmoidal dose-response. FIG. 6 is a line graph showing a ciliary beating frequency (CBF) calibration curve. The results from our CBF measurement system are similar to the results obtained from fast cinematography (a standard method). A cross-section image of cylindrical nanopores formed in p++ Si is shown in FIG. 7, according to prior art by Janshoff et al., 1998. Similarly, FIG. 8 shows that porous size varies with applied current; p++ Si, HF (aq):EtOH=3:1, according to the prior art of Janshoff et al, 1998. FIG. 9 illustrates patterned airway epithelial cell layers trapped on porous silicon support. FIG. 10 is a schematic diagram for incorporation of airway epithelial cell layers grown on porous silicon into a microfluidic device or flow chamber. FIG. 11 depicts a sensing device for cell physiological parameters. The device has a gas or fluid perfusion path, a media perfusion path, Snapwell, and four electrodes (Harvard Apparatus, Holliston, Mass.).

Airway Epithelial Cell Physiology

About 1,000 to 21,000 liters of air pass through the human airway system each day (Wanner et al., 1996). Airway lining epithelial cells provide first line of protection and response for inhaled harmful agents such as dusts, air pollutants, chemicals and microbes as well as biological/chemical warfare agents. Ciliated cells and goblet cells are the major types of airway lining epithelial cells. Ciliated cells and goblet cells play a major role in the protection mechanisms of the airways. Airway goblet cells secret mucins forming protective mucous layer in the airways and ciliated cells are responsible for the clearance of mucous materials. Both types of cells interact with each other to provide a major defense mechanism for the airways—mucociliary clearance. Airway ciliated cells and goblet cells can be stimulated by various factors such as pH, cigarette smoke, air pollutants, organic solvents and toxins and their responses are rapid, usually in the range of seconds (Rivera, 1962; Wanner et al., 1996; Flo-Neyret et al., 2001). The major response for ciliated cells is the change of ciliary beating frequency (CBF), while goblet cells respond by the secretion (exocytosis) of mucins. In this project, we plan to use these physiological responses of ciliated and goblet cells as an indicator for detecting suspected harmful agents in the air.

Airway epithelial cells reside on the surface of the airways and require the air-fluid interface environment to maintain normal physiological functions (Karp et al., 2002). These characteristics make the airway epithelial cells an ideal choice for cell-based airborne harmful agent detection sensors that need direct air contact for gaseous samples.

Airway Epithelial Cell Culture

Airway epithelial cells are collected from rabbits as described previously (Nguyen et al., 1998; Chin et al., 2002; Karp et al., 2002). The detailed methods for culturing the airway epithelial cells in the air fluid interface have also been previously published (Karp et al., 2002). Briefly, Transwell™ inserts of supporting materials for cell growth are coated with collagen (60 ug/ml) for 18 hours before use. Then, phosphate buffer saline (PBS) is used to rinse the membrane of the inserts to remove the remaining liquid before the airway epithelial cells are seeded. It requires approximately 5–7 days under appropriate incubation, as known in the art, to develop a functional epithelial cell layer in the air/fluid interface (Karp et al., 2002).

Differentiated airway epithelial cells respond to changes in environmental factors or contact with infectious agents, resulting in changes to their physiological parameters such as transepithelial resistance (TER), ciliary beat frequency in ciliated cells (CBF) and secretion of mucins from goblet cells.

Transepithelial Resistance (TER)

An epithelial cell monolayer is cultured on a polystyrene porous membrane in Transwell™ plates (Corning Costar). Airway epithelial cells are grown at the interface of air and liquid. Culture cell support medium is provided from the bottom through the porous membrane. The TER of airway epithelial cell monolayer cultured in Transwell™ can be monitored using a portable Coltohmmeter (Millipore, Bedford, Mass.) attached to a dual "chopstick" or transcellular resistance measurement chamber (Millipore, Bedford, Mass.) (FIG. 2). Each of the two electrode systems contains Ag/AgCl electrode for measuring voltage and a concentric spiral of silver wire for passing current across the epithelium. The electrode system is presterilized with 70% ethanol before use in order to maintain cell culture sterility. To measure electrical properties, 300–400 µL of culture media is placed on the apical surface. Current can then be pushed across the epithelium to measure TER (ohms.cm$^2$). TER values higher than the background fluid resistance indicate a confluent airway epithelium with tight junctions as shown in FIG. 3.

Detection of Mucin Secretion from Airway Goblet Cells

Quinacrine is a fluorescent dye specifically accumulated in the acidic secretory granule of airway goblet cells (FIG.

4). Airway goblet cells store mucin in their secretory granules before its release. Accordingly, this unique property of quinacrine can be used to monitor the secretion of goblet cells in the invention. A similar approach was successfully applied to monitor mucin secretion in goblet cells in traditional culture conditions (FIG. 4; Kolber & Henkart, 1988; Bittner, 1999). Cells are stained in 100 µM quinacrine for 5 min. Quinacrine-labeled cells are stimulated with varying concentrations of ATP or UTP (1 uM to 3 mM). The cell support medium is then collected from the micro-device and saturated-Tris (diluted 1/50) is added to maximize fluorescent emission of the quinacrine (Kolber & Henkart, 1988). The fluorescence of these samples was read on a spectrofluorophotometer with an excitation wavelength of 410 nm and an emission wavelength of 500 nm (FIG. 5).

Instantaneous On-Line Measurement of Airway Ciliary Beating Frequency (CBF)

We developed an on-line system to monitor CBF for airway ciliated cells. This measuring system is based on a previously described method, that has been modified to measure on-line ciliary beating of single ciliated cells (Ben-Shimol et al., 1991; Sanderson & Dirksen, 1995; Nguyen et al., 2001). The apparatus consists of a Nikon Diaphot inverted microscope with a 100×, 1.4 NA oil immersion objective and a DC illumination source. Images were captured by thermoelectrically cooled, low dark noise (1.3 photoelectrons/sec/pixel at 36° C.) digital camera with a 336×243 CCD matrix, a 16-bit pixel resolution, and a readout rate of 100 Kpixel/sec (Spectra Source Model 400, Westlake Village, Calif.).

The camera was mounted in the photoport of the microscope using a 20× relay lens yielding a 10 pixels/µm resolution. To increase the sampling rate, we avoided capturing the whole image. Instead, single line scans were sampled at a rate of 256 scans/sec and on-line fast Fourier transform of the line samples gives the CBF. Each scan sampled an area 0.2×30 µm across the optical field of the ciliated cells. The CBF from this digital photography method was calibrated against manual counting of ciliary beating of images captured with fast cinematography (128 pictures/sec). The CBF obtained by the two techniques yielded the same beat frequency over the ranges of 0. to 28 Hz (Nguyen et al., 2001; FIG. 6). Since this measuring system is based on the optical signals, it can be easily integrated into the micro-devices used in the invention without disruption of micro-fluidic channels.

Build Air-Liquid Interface in Microfluidic Devices

Silicon is a preferred material for this application. In particular silicon has been utilized to: (1) allow immobilization of extracellular matrix molecules through protein adsorption or silane chemistry, (2) form large pores (10s of microns) by wet or dry etching techniques and (3) form nanoporous structures and membranes by electrochemical etching. Nanoporous silicon has been extensively studied for electronic biosensing application and is formed as follows:

Porous Si samples were prepared by anodically etching p+ type silicon (5–10 W.cm resistivity, <1-O-0> orientation, B-doped, Silicon Quest Inc.) in an ethanolic hydrofluoric (HF) solution (HF-ethanol 1:1, v/v)). A mesh Pt counter electrode was used to ensure a homogenous electric field. Nanoporous and crystalline Si samples were rinsed with ethanol, dried under nitrogen stream, and exposed to ozone for 15 minutes (Janshoff et al., 1998).

Incorporate Airway Epithelial Cells into Microfluidic Device

Airway epithelial cells are cultured on silicon grooves prepared in the following procedure. Porous Si samples are prepared by anodically etching p-type silicon (5–10 Ω/cm-.resistivity, (100) orientation, B-doped, supplied by silicon Quest Inc.) in a 1:1 v/v mixture of ethanol and aqueous hydrofluoric acid (49%) at 5 mA/cm$^2$ for 2 minutes in the absence of light. A mesh Pt counter electrode is used to ensure a homogenous electric field. Each sample is then rinsed thoroughly with ethanol and dried under a nitrogen stream. Crystalline Si samples are rinsed with ethanol and dried under a nitrogen stream. Both types of Si samples are exposed to ozone for 15 min using an ozone generator (Ozomax, Quebec, Canada) with a flow rate of 8 g/h of $O_3$ to provide a stable, oxidized, silanol-terminated surface. Prior to cell seeding, Si samples are cleaned by exposure to oxygen plasma on a Technics 500 II Asher at a base vacuum of 80 mtorr and $0_2$ pressure of 120 mtorr at a power of 100 W for 4 min. Samples are rinsed four times in (Vitrogen, Cohesion Technologies, Palo Alto, Calif.) for 1.5 h at 37° C. As a control, collagen I is also adsorbed to polystyrene cell culture wells. 0.1% bovine serum albumin (BSA) is used to prevent cell adhesion on the non-grooved surface. Epithelial cells are seeded in culture medium and allowed to attach to overnight. Top layers of cells are exposed to air. The medium is presaturated by 5% $CO_2$. The airway epithelial cells are allowed to differentiate, and physiological parameters are monitored by measuring TER, CBF and mucin secretion.

Patterned airway epithelial cells can be generated by the above protocol. Once airway epithelial cell layers are established on porous silicon, the physiological parameters of the airway epithelial cells are measured on a porous silicon disc inserted into the Transwell™ culture plate (FIG. 10). Finally, an airway cell-based biosensor on a porous disc is incorporated into the chamber as shown in FIG. 10. The chambers create an environment in which the apical surface of the airway epithelial cell layer is exposed to atmospheric air and gases while the basolateral surface is perfused with medium (FIG. 10). Physiological parameters are monitored biologically and electronically, as described herein.

Physiology of Airway Epithelial Cells in Microfluidic Devices

The following physiological conditions of the epithelial cells are measured in the micro-fluidic devices.

Viability. Commercial available kits (LIVE/DEAD Viability/Cytotoxicity Kit, Molecular Probes, Eugene, Oreg.) are used to determine the viability (live/dead) state of the cultured epithelial cells.

Cell proliferation is monitored by the various methods set forth below.

MTS calorimetric method: MTS (3(4,5-dilnethylthiazol-2-yl)-S-( )-carboxymethoxy-phenyl)-2-(4-sulfophenyl-2H-tetrazolium)) can be reduced by cells into a soluble formazan product that has absorbance at 490 nm. This conversion is accomplished by using dehydrogenase enzymes found in metabolically active (live) cells. The absorbance at 490 nm (the quantity of formazan) is proportional to the number of living cells. The method is used to determine the cell number in the cell-aggregate based sensor devices. A commercially available kit (CellTiter 96® Aqueous Assay) can be purchased from Promega (Madison, Wis.).

BrdU Incorporation: incorporation of 5-bromo-2'.deoxyuridine (BrdU) into newly synthesized DNA is used to test cell proliferation for the cells grown on surfaces. BrdU is a thymidine analog incorporated into proliferating cells and thus permits indirect detection of rapidly proliferating cells with fluorescent labeled anti-BrdU antibodies. A commercially available BrdU kit can be purchased from Molecule Probes (Eugene, Oreg.).

TUNEL Assay: DNA fragmentation that occurs during the later stage of apoptosis. TUNEL (terminal deox)nucleotidyl transferase dUTP nick end labeling) assays are widely used for detecting DNA fragmentation in apoptotic cells.

Annexin V: surface phosphatidylserine (PS) is an indicator of intermediate stages of apoptosis. Highly fluorescent annexin V conjugates that bind to PS provide a quick and reliable detection method to identify apoptotic cells. Both the above assay kits can be purchased from Molecule Probes (Eugene, Oreg.).

Monitor Physiological Response to External Stimuli (i.e. Airborne Pathogen) in Microfluidic Device Physiological Responses of Airway Epithelial Cells ATP is used to stimulate the epithelial cells in the microdevices to investigate if these cells still maintain the capacity of normal physiological responses. The normal responses of ATP stimulation include CBF increase in ciliated cells' and mucin secretion increase in goblet cells. Both responses are monitored with the methods described previously (FIGS. 5 and 6 on page 7).

Most traditional cell-based biosensors detect harmful agents by monitoring the cytotoxic effects. However, it usually takes hours, even days before noticeable cytotoxicity can be detected. The responses of airway epithelial cells to harmful agents can be very fast in the range of seconds to minutes (mucin secretion and CBF change, for example), or in the ranges of hours (TER change). Airway epithelial cells, thus, provide two sets of responses in different time frames that enhance the versatility of detection in the micro-devices of the invention.

TER (Trans Epithelial Resistance)

The electrical resistance and electrical potential difference has been measured across isolated airway (ciliary) epithelium. The methods used for dissection and mounting of the tissue are described above, and summarized in FIG. 11. Our airway epithelial cell patterned silicon disc (FIG. 11) is put into snap well which is inserted into the chamber. Cells are exposed to an air-liquid interface which occurs in the normal in vivo environment such as with nasal and pulmonary cells. The chambers create an environment in which the apical surface of the airway epithelial cell layer is exposed to air or gases while the basolateral surface is perfused with medium (FIG. 11). TER is monitored by four Ag/AgCl electrodes (two for upper and two fo lower chamber). A decrease of TER indicates the cells have been exposed to a harmful biological or chemical agent.

Ciliary Beating Frequency (CBF)

CBF change is monitored using a system previously developed (Nguyen et al., 2001; results of such monitoring are shown in FIG. 6). A change (decrease or increase) in CBF is a sign of the presence of a harmful agent and exposure of the cells thereto (Riveria, 1962; Warnner et al., 1996; Flo-Neyret et al., 2001).

Mucin Secretion

Mucin secretion from goblet cells is monitored using a known method (Kolber and Henkart, 1998; Bittner, 1999; FIG. 5). Results of such monitoring method are shown in FIG. 5. The increase in mucin secretion from goblet cells indicates the presence of airborne harmful agents (Konaradova, 1995; Wannex et al., 1996; Flo-Neyret et al., 2001).

Long Term Stability of Cell Viability and Function in Microfluidic Device

Monitoring the physiological conditions (viability, proliferation and apoptosis) and responses (TER, CBF and mucin secretion) of epithelial cells in the microdevices at different time points to investigate the physiological conditions. Currently, the short "shelf-life" is a major disadvantage for many cell-based sensors. The data collected here will be used to assess the long-germ stability and viability of our epithelial cell microdevices. The date obtained from long-term monitoring of the airway epithelial cells is critical for the development of a longer "shelf-life" biosensor.

Accordingly, in the drawings and specification there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A method of monitoring an air atmosphere for a presence of a harmful biological or chemical agent, the method comprising:
    providing a plurality of mammalian respiratory airway epithelial cells borne on a porous support;
    contacting the porous support with a cell nutrient medium and with air by positioning said porous support at an air-liquid interface between the cell nutrient medium and the air;
    sampling the air atmosphere to thereby create an air flow over the air-liquid interface so that the respiratory epithelial cells borne on the porous support are contacted by the sampled air; and
    monitoring the respiratory epithelial cells for at least one physiological parameter indicating the cells have been exposed to the harmful agent.

2. The method of claim 1, wherein the plurality of mammalian respiratory airway epithelial cells consists of rabbit cells.

3. The method of claim 1, further comprising sufficient cell nutrient medium in contact with at least a lower surface of the porous support to nourish the plurality of respiratory airway epithelial cells.

4. The method of claim 1, wherein the porous support comprises silicone.

5. The method of claim 1, wherein the porous support comprises a nanoporous silicone composition.

6. The method of claim 1, wherein the porous support consists of a nanoporous silicone composition having pores no larger than one micrometer in diameter.

7. The method of claim 1, wherein the porous support comprises a silicone composition having pores consisting of a sufficiently small diameter to prevent the plurality of mammalian respiratory airway epithelial cells from entering the pores.

8. The method of claim 1, wherein the porous support comprises a nanoporous silicone composition having an average pore size smaller than the average size of the plurality of mammalian respiratory airway epithelial cells.

9. The method of claim 1, wherein the plurality of mammalian respiratory airway epithelial cells comprises a confluent layer of cells.

10. The method of claim 1, wherein the plurality of mammalian respiratory airway epithelial cells comprises a monolayer of cells.

11. The method of claim 1, wherein the plurality of mammalian respiratory airway epithelial cells comprises ciliated cells and goblet cells.

12. The method of claim 1, wherein the plurality of mammalian respiratory airway epithelial cells comprises ciliated cells and goblet cells and the at least one physiological parameter monitored comprises ciliary beating frequency of the ciliated cells.

13. The method of claim 1, wherein the plurality of mammalian respiratory airway epithelial cells comprises ciliated cells and goblet cells and the at least one physiological parameter monitored comprises an electrical response of the plurality of mammalian respiratory airway epithelial cells.

14. The method of claim 1, wherein the plurality of mammalian respiratory airway epithelial cells comprises ciliated cells and goblet cells and the at least one physiological parameter monitored comprises mucin secretion from the goblet cells.

15. The method of claim 1, wherein the harmful biological or chemical agent comprises a toxin.

16. The method of claim 1, wherein the harmful biological or chemical agent comprises a biological warfare agent.

17. The method of claim 1, wherein the harmful biological or chemical agent comprises a chemical warfare agent.

18. A method of monitoring an air atmosphere for a presence of a harmful biological or chemical agent, the method comprising:
    providing a porous support having an upper surface and a lower surface, and having a plurality of channels etched on the upper surface of the porous support;
    contacting the porous support with a cell nutrient medium and with air by positioning said porous support at an interface between the cell nutrient medium and the air so that the lower surface of the support is in contact with the cell nutrient medium and so that the upper surface of the support is in contact with the air;
    seeding a plurality of mammalian respiratory airway epithelial cells into the plurality of channels etched on the upper surface of the porous support;
    sampling the air atmosphere to thereby create an air flow over the upper surface of the porous support so that the plurality of mammalian respiratory airway epithelial cells seeded into the etched channels are contacted by the sampled air; and
    monitoring the plurality of mammalian respiratory airway epithelial cells for at least one physiological change indicating the cells have been exposed to the harmful agent.

19. The method of claim 18, wherein the plurality of mammalian respiratory airway epithelial cells are primary rabbit cells.

20. The method of claim 18, further comprising sufficient cell nutrient medium in contact with a lower surface of the porous support to nourish the airway epithelial cells.

21. The method of claim 18, wherein the porous support comprises silicone.

22. The method of claim 18, wherein the porous support comprises a nanoporous silicone composition.

23. The method of claim 18, wherein the porous support consists of a nanoporous silicone composition having pores no larger than one micrometer in diameter.

24. The method of claim 18, wherein the porous support comprises a silicone composition wherein the pores consist of a sufficiently small diameter to prevent the plurality of mammalian respiratory airway epithelial cells from falling thereinto.

25. The method of claim 18, wherein the porous support comprises a nanoporous silicone composition having an average pore size smaller than the average size of individual cells in the plurality of mammalian respiratory airway epithelial cells.

26. The method of claim 18, wherein the plurality of mammalian respiratory airway epithelial cells comprises a confluent layer of cells.

27. The method of claim 18, wherein the plurality of mammalian respiratory airway epithelial cells comprises a monolayer of cells.

28. The method of claim 18, wherein the plurality of mammalian respiratory airway epithelial cells comprises ciliated cells and goblet cells.

29. The method of claim 18, wherein the plurality of mammalian respiratory airway epithelial cells comprises ciliated cells and goblet cells and the at least one physiological parameter monitored comprises ciliary beating frequency of the ciliated cells.

30. The method of claim 18, wherein the plurality of mammalian respiratory airway epithelial cells comprises ciliated cells and goblet cells and the at least one physiological parameter monitored comprises an electrical response of the plurality of mammalian respiratory airway epithelial cells.

31. The method of claim 18, wherein the plurality of mammalian respiratory airway epithelial cells comprises ciliated cells and goblet cells and the at least one physiological parameter monitored comprises mucin secretion from the goblet cells.

32. The method of claim 18, wherein the harmful biological or chemical agent comprises a toxin.

33. The method of claim 18, wherein the harmful biological or chemical agent comprises a biological warfare agent.

34. The method of claim 18, wherein the harmful biological or chemical agent comprises a chemical warfare agent.

* * * * *